United States Patent [19]

Emerit

[11] 4,287,819

[45] Sep. 8, 1981

[54] SOURCE OF VACUUM AND DEVICE FOR MAINTAINING A NEGATIVE PRESSURE IN AN ENCLOSURE

[76] Inventor: André A. C. Emerit, 30 Rue du Docteur Roux, 95110 Sannois, France

[21] Appl. No.: 957,286

[22] Filed: Nov. 2, 1978

[30] Foreign Application Priority Data

Nov. 9, 1977 [FR] France ............................... 77 33716
Aug. 2, 1978 [FR] France ............................... 78 22802

[51] Int. Cl.³ .................... A61M 1/00; B65B 31/04; B65D 81/20; F04B 21/00
[52] U.S. Cl. ....................................... 99/472; 73/731; 116/DIG. 9; 128/278; 128/297; 128/765; 141/65; 215/230; 215/260; 215/311; 215/365; 417/437; 417/555 R
[58] Field of Search ............... 417/490, 497, 555, 545, 417/437; 4/255, 257; 92/100; 215/260, 365, 230, 311, 312; 116/DIG. 9, 266; 73/731, 146.8, 146.2; 53/510; 141/65; 220/85 B; 128/760, 763, 765, 276, 278, 297, 220, 237, 234; 433/91, 92; 99/472

[56] References Cited

U.S. PATENT DOCUMENTS

| | | | |
|---|---|---|---|
| 578,410 | 3/1897 | Lord | 99/472 |
| 1,556,981 | 10/1925 | Voight | 141/65 |
| 2,436,849 | 3/1948 | Billetter | 141/65 |
| 3,135,411 | 6/1964 | Osborne | 215/312 X |
| 3,452,708 | 7/1969 | Richardson | 73/146.8 X |
| 3,800,780 | 4/1974 | Elliott | 128/276 |
| 3,980,082 | 9/1976 | Miller | 73/731 X |

FOREIGN PATENT DOCUMENTS

| | | | |
|---|---|---|---|
| 599822 | 10/1934 | Fed. Rep. of Germany | 99/472 |
| 565067 | 1/1924 | France | 417/437 |
| 886540 | 10/1943 | France | 99/472 |
| 54924 | 8/1923 | Sweden | 128/297 |
| 1061801 | 3/1967 | United Kingdom | 215/365 |

Primary Examiner—Leonard E. Smith
Attorney, Agent, or Firm—Irons and Sears

[57] ABSTRACT

The source of vacuum comprises a tubular body in which a piston which is combined with a piston rod is axially slidable. A seal is interposed between the rod and the body where the rod extends out of the body. A suction orifice is provided which is on the axis of or in the vicinity of the axis of the body and parallel to the axis. An arrangement is provided for holding the body and urging the piston to one end of the body in one hand. A communication passage is provided for putting the suction orifice in communication with a chamber defined between the piston and the body when the piston is depressed relative to the body.

13 Claims, 16 Drawing Figures

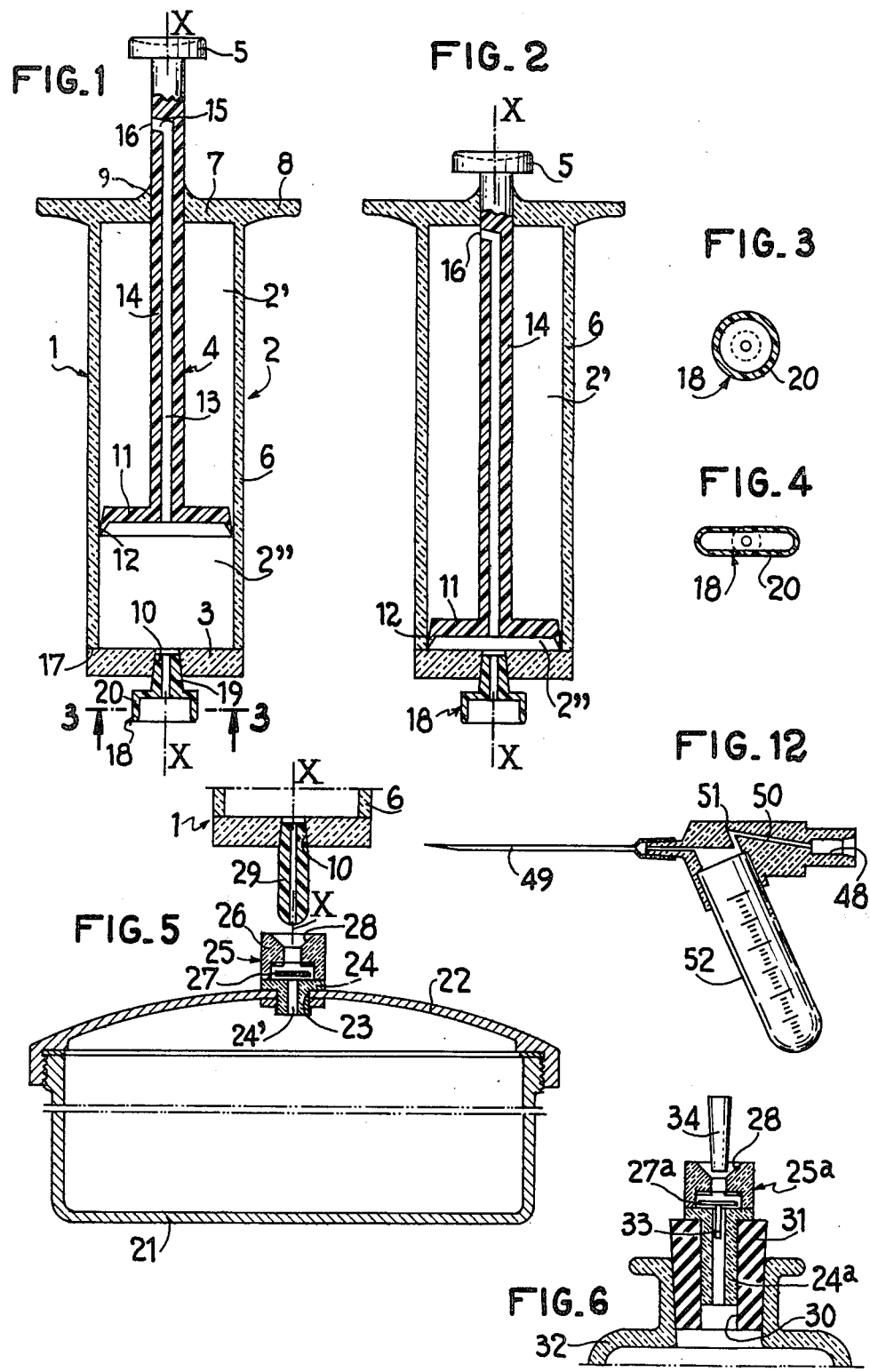

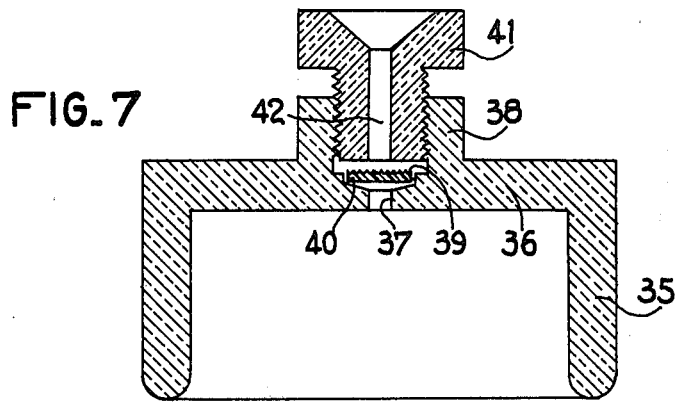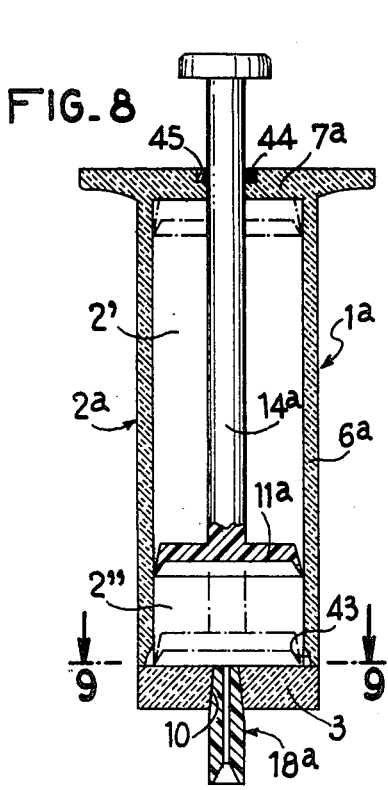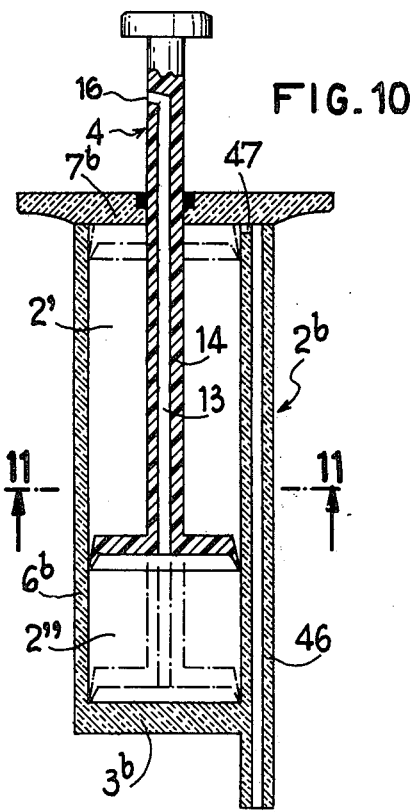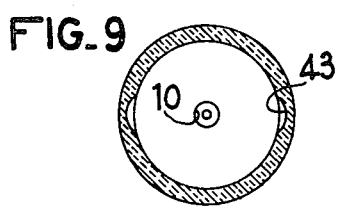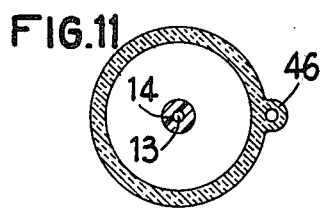

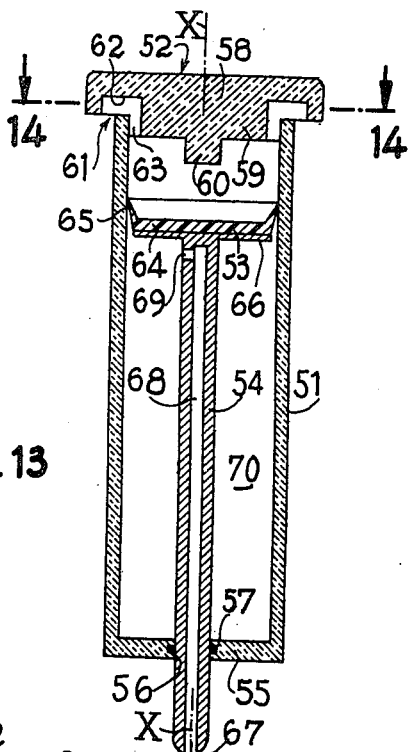
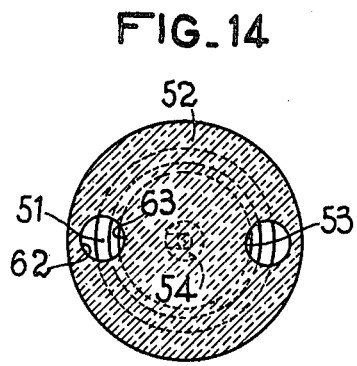
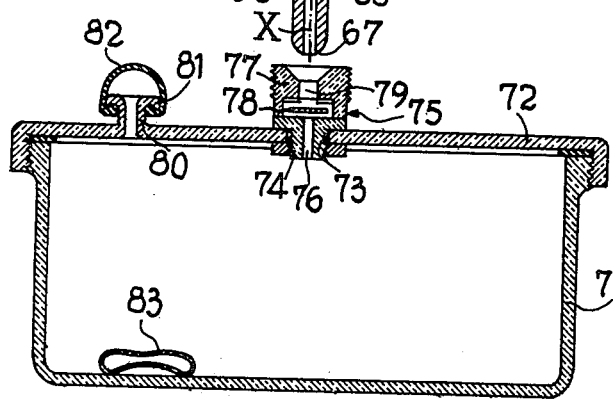
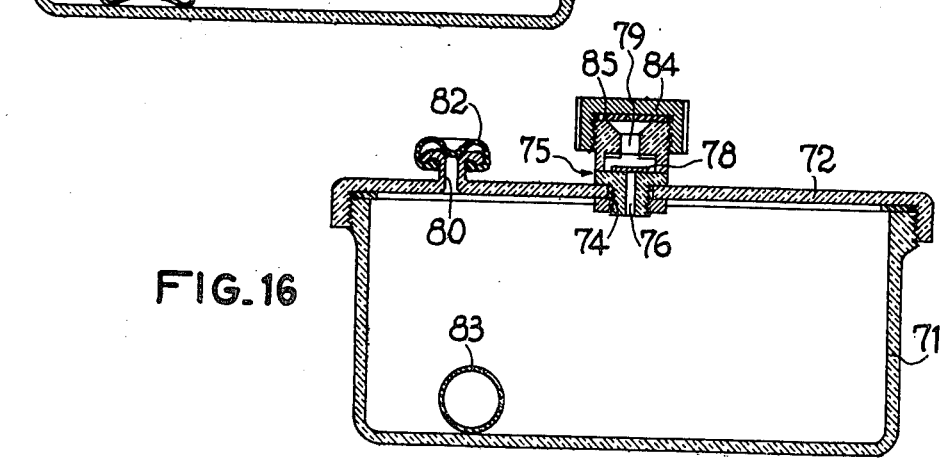
FIG._13
FIG._14
FIG._15
FIG._16

SOURCE OF VACUUM AND DEVICE FOR MAINTAINING A NEGATIVE PRESSURE IN AN ENCLOSURE

DESCRIPTION

The present invention relates to sources of vacuum.

An object of the invention is to provide a portable source of vacuum whereby it is possible in particular to exert a suction on oneself at practically any point of the body for the purpose of drawing off the venom of a sting or bite after having applied the suction orifice in a sealed manner on the skin.

For this purpose, the source of vacuum according to the invention comprises: a tubular body in which is slidable a piston connected to a rod which extends through a sealed aperture of a first end of the body, a suction orifice located on the axis or in the vicinity of and parallel to the axis of the body, means for holding the body and driving the piston toward a second end of the body with one hand, and communication means for putting the suction orifice in communication with a chamber of the body adjacent the first end when the piston is depressed.

In one embodiment, the body has two radial ears in the vicinity of the first end, the suction orifice is formed in the second end of the body and said communication means put the suction orifice suddenly in communication with said chamber of the body when the piston reaches a predetermined position. According to another embodiment, whereby it is possible to regulate the negative pressure obtained, the communication means permanently put the suction orifice in communication with said chamber.

In the latter case, the invention provides in particular an embodiment which is more particularly adapted for certain applications, such as the creation of a partial vacuum in a jar or the like which has a cover provided with a check-valve and is placed on a table or a shelf. In this source of vacuum, the body may be held fully in one hand, and the rod of the piston is provided with an axial passageway which extends from its free end to the vicinity of the piston where it communicates with said chamber of the body by way of a radial orifice, the second end of the body being provided with venting means.

The source of vacuum according to the invention may be in particular employed in combination with a device for creating and maintaining a negative pressure in an enclosure comprising a check valve connected to a wall of the enclosure and means for connecting the valve to a source of vacuum, these means comprising a screwed coupling which presses the closure member of the valve against its seat when it is completely screwed in position.

In order to check the maintenance of the negative pressure, according to another feature of the invention, there may be provided an elastically deformable membrane which is subjected on a single side thereof to the pressure prevailing in the enclosure.

Further features and advantages of the invention will be apparent from the ensuing description which is given solely by way of example with reference to the accompanying drawings in which:

FIG. 1 is a longitudinal sectional view of a source of vacuum according to the invention;

FIG. 2 is a view similar to FIG. 1 of the same source of vacuum in the suction position;

FIG. 3 is a sectional view taken on line 3—3 of FIG. 1;

FIG. 4 is a view similar to FIG. 3 of a modification;

FIGS. 5 to 7 are partial sectional views of devices according to the invention for creating and maintaining a negative pressure;

FIGS. 8 and 10 are longitudinal sectional views of two other embodiments of a source of vacuum according to the invention;

FIGS. 9 and 11 are respectively cross-sectional views taken on lines 9—9 and 11—11 of FIGS. 8 and 10;

FIG. 12 is a sectional view of a device for drawing off blood of utility in particular with the source of vacuum shown in FIGS. 10 and 11;

FIG. 13 is an axial sectional view of a source of vacuum according to another embodiment of the invention;

FIG. 14 is a sectional view taken on line 14—14 of FIG. 13;

FIG. 15 is an axial sectional view of a jar provided with two checking devices according to the invention, and, FIG. 16 is a view similar to FIG. 15 of the jar after a negative pression has been created therein.

The source of vacuum or syringe 1 shown in FIGS. 1 and 2 comprises four members: a body 2, a cap 3 and piston-rod unit 4 provided with an actuating knob 5. Each of these members is made from moulded plastics material.

The body 2 has a generally cylindrical shape having an axis X—X and comprises a tube 6 at one end of which is provided a flat end portion 7 and two outer radial ears 8. For convenience of description, it will be assumed that the axis X—X is vertical and that the end portion 7 and the ears 8 are at the upper end of the tube 6. The other end of the latter is open.

The end portion 7 is provided with a central orifice 9 whose upper part is constricted by a relatively flexible thin flange.

The cap 3 is a disc whose outside diameter is equal to that of the tube 6 and comprises at its centre an upwardly convergent orifice 10.

The piston 11 has on its periphery a divergent annular lip portion 12 of short axial extent and extending downwardly. An axial passageway 13 extends from the lower face of this piston through the major part of the length of the rod 14 and terminates in an elbow 15 and radially opens out by way of a vent 16. The diameter of the rod 14 is roughly equal to that of the lower part of the orifice 9 of the end portion 7.

The syringe 1 is assembled in the following manner:

The rod 14 is inserted in the tube 6 through the bottom of the latter and made to pass through the orifice 9. The flange of the latter is then deformed upwardly and forms an annular lip portion 9 which hermetically bears against the rod 14 while it allows the sliding of the latter, with the lip portion 12 of the piston 11 sliding hermetically against the inner wall of the tube 6. The knob 5 is then secured, for example by adhesion, to the upper end of the rod 14 and the cap 3 is likewise secured to the lower planar end face 17 of the tube 6.

This syringe operates in the following manner:

With the piston in the upper position, the syringe is held in one hand in the conventional manner with two fingers under the ears 8 and the thumb on the knob 5. The latter is depressed and this causes the piston to descend. The air under the piston escapes to the atmosphere by way of the passageway 13 and the vent 16. Possibly, it may also escape by way of the orifice 10 if the latter is opened to the atmosphere.

At the end of the travel of the piston, when the latter abuts against the cap 3, the vent 16 passes just below the end portion 7 (FIG. 2). The chambers 2' and 2" of the body are then put into communication with each other by way of the passageway 13 so that the vacuum created in the upper chamber 2' by the descent of the piston produces a sudden negative pressure in the lower chamber 2" the volume of which is at this moment very small.

An end member 18 may be fitted in the orifice 10, this member 18 comprising a frustoconical upper connector 19 provided axially with a cylindrical lower skirt portion 20 which is open on the underside and connected to the connector 19 by a flange. if this skirt portion is applied on a wound, a bite or a sting before the piston 11 has been shifted downwardly, or at least before the piston reaches the cap 3, the end of the descent of the piston results in a sudden suction whereby it is possible to draw off the locally soiled blood. This first aid may be carried out on oneself in a very convenient manner on practically any part of the body, since one hand is sufficient to create the suction.

FIGS. 3 and 4 show two modifications of the section of the skirt portion 20, one being circular and the other oblong, which may be used as desired in accordance with the shape of the wound to be treated.

FIG. 5 shows a container 21 for preserving a product, for example a food product, under a partial vacuum. This container is provided with a screwed lid 22 provided with a central aperture 23 in which the lower portion 24 of a check-valve 25 is fixed. This lower portion comprises a passageway 24' and a planar upper surface on which the periphery of an upper member 26 is hermetically fixed. The member 26 defines with the portion 24 a cavity for a planar free closure member 27. This cavity communicates at the upper end with the exterior by way of a passageway 28 which is cylindrical and then divergent. The upper surface of the cavity is planar but grooved.

In order to create a negative pressure in the container 21, there is fitted in the orifice 10 of the syringe 1 an end member 29 which has a longitudinal passageway and a rounded end portion. This end portion is applied in the opening of the passageway 28 and the piston of the syringe is fully depressed. The negative pressure thus produced raises the closure member 27 and the grooves of its cavity allow the air to escape. It will be understood that the operation may be carried out several times for the purpose of increasing the negative pressure in the container 21, the value of the negative pressure merely being limited by the degree of fluidtightness of the various parts. Thus it is very simple to preserve food in the container under a vacuum.

The valve $25^a$ shown in FIG. 6 is on the whole similar to the preceding valve but its lower portion $24^a$ is longer and is fitted in the passageway 30 of a flexible stopper 31 of a jar 32 or the like. Moreover, the closure member $27^a$ is provided with a lower guide rod 33 which slides with clearance in the passageway of the portion $24^a$. The operation is the same as that of the embodiment shown in FIG. 5 and may, for example, serve to preserve under a vacuum products in a laboratory. In both cases, in order to compensate for any defective seal afforded by the closure member, the passageway 28 may be closed by a stopper, for example a frustoconical flexible stopper 34 after the negative pressure has been created.

FIG. 7 shows a medical suction-producing cupping member comprising a cylindrical body 35 the upper end of which is closed by an end portion 36 whereas the lower end is open, the end portion being provided with a centre orifice 37. Upwardly projecting from the end portion 36 is a coaxial tapped tube 38. A counter-bore 39 surrounds the orifice 37 and receives the closure member 40 which is a planar disc whose height exceeds the depth of the counter-bore and is grooved on its upper side. The cupping member is completed by a connector 41 which is screwed in the tube 38. This connector has a planar lower face and an axial passageway 42 whose upper open portion is divergent. In order to place the cupping member on the back of a patient, the connector 41 is slightly unscrewed so as to allow a small vertical clearance for the closure member 40 as shown in FIG. 7. The end of the end member 29 mounted on the syringe 1 is inserted in the passageway 42 and the piston 11 is depressed fully. The grooves of the closure member 40 allow the air to escape. The cupping member is very easily and quickly mounted. If the seal is desired to be guaranteed for a long period, the connector 41 is screwed until it abuts against the periphery of the counter-bore 39 and slightly crushes the closure member. By way of a modification, the disc 40 may be replaced by a ball.

The syringe $1^a$ shown in FIGS. 8 and 9 differs from that shown in FIGS. 1 and 2 by the fact that the rod $14^a$ of the piston $11^a$ is solid and the inner wall of the tube $6^a$ has two axial notches 43 adjacent the cap 3. Moreover, a seal is provided between the rod $14^a$ and the end portion $7^a$ by means of an O-ring 44 disposed in a groove 45 in this end portion. There is moreover shown an end member $18^a$ fitted in the orifice 10 and having a roughly cylindrical elongated shape, the central passageway of this end member being divergent at its lower end. The end member $18^a$ may be in particular employed for treating small stings.

The syringe $1^a$ produces, in the same way as the syringe 1, a sudden negative pressure at the end of the travel of the piston by putting two chambers 2', 2" of the body $2^a$ of the syringe in communication with each other when the lip portion of the piston arrives in a position in front of the notches 43. Consequently, these two syringes may be employed for the same uses. Note that, in this embodiment, it is necessary to bring the piston near to the notches 43 before connecting the syringe to the object to be subjected to suction in order to allow the evacuation of the air from the chamber 2".

In some cases, the suddenness of the creation of the negative pressure may be undesirable, for example for taking off blood. The syringe $1^b$ shown in FIGS. 10 and 11 enables an adjustable progressive negative pressure to be obtained. A conduit 46 extends along the tube $6^b$ and communicates with the chamber 2' by way of a radial orifice 37 adjacent the end portion $7^b$ and extends downwardly beyond the cap $3^b$, the latter being devoid of a central orifice. FIG. 10 shows a syringe body $2^b$ comprising two moulded parts which are assembled by planar surfaces. The piston-rod unit 4 is the same as that shown in FIG. 1.

When the piston is brought from its upper position to any position, such as that shown in FIG. 10, it creates in the chamber 2' a negative pressure which is transmitted by way of the conduit 46. For example, the latter may be connected to the entrance 48 of the blood taking device of FIG. 12, which is connected to a hollow needle 49 through a conduit 50 having a labyrinth 51. A graduated tube 52 is connected between the labyrinth 51 and the needle 49. The negative pressure produced by the movement of the piston depends on the position of the latter and determines the drawing off of the desired amount of blood in the tube 52.

Note that, for maximum negative pressure, the vent 16 is in the chamber 2', so that the piston is subjected to the same pressure on both sides thereof and has no tendency to rise. By way of a modification, the vent could be located on the rod 14 so as to be always above the end portion $7^b$, or the rod could be solid as in FIG. 8 and the cap $3^b$ provided with an orifice allowing the air in the chamber 2" to escape.

Of course, it is possible to envisage very many applications of the syringes shown in FIGS. 1, 8 and 10 which may be used whenever it is desired to create a negative pressure rapidly and conveniently with a source of vacuum which is small and always available, in particular at home or in the laboratory: clearing of small obturated pipes, the priming of water traps, transfer of dangerous fluids between two vessels, etc..

The source of vacuum shown in FIGS. 13 and 14 comprises three elements, namely a body 51, a cover 52 and a piston 53 connected to a piston rod 54.

The body 51 is cylindrical and has an axis X—X which will be assumed to be vertical for convenience of description. Its lower end is formed by an end wall portion 55 provided with a central orifice 56. The latter is provided with an annular groove in which is disposed an O-ring 57 for sealing purposes. The upper end of the body 51 is open.

The cover 52 comprises, geometrically, a disc 58 whose diameter exceeds the outside diameter of the body 51 and whose lower surface is applied coaxially against the upper end edge of the body 51. The cover 52 is held in position by a cylindrical centre portion 59 which extends downwardly from the disc 58 and is a close fit in the upper end of the body 51. A central spigot 60 projects downwardly from this part 59.

Two diametrally opposed vents 61 are provided in the cover 52. Each one thereof is formed by a recess 62 formed in the lower side of the disc 58 so as to extend across the wall of the body 51. This recess is extended downwardly in the radially inner part thereof by a groove 63 which extends through the thickness of the part 59 of the cover. Thus, each vent 61 has an L-shaped axial section (FIG. 13) and a circular section in plan (FIG. 14). It puts the interior of the body 51 permanently in communication with the atmosphere.

The piston 53 comprises a solid end 64 around which extends a flexible skirt portion 65 which extends upwardly and slides on the inner surface of the cylindrical wall of the body 51. The height of the skirt portion 65 exceeds the height of the spigot 60. The end portion 64 is secured to a circular end plate 66 of the rod 54. The latter extends through the orifice 56 and has a hemispherical free end portion 67 which is located below the end of the body irrespective of the position of the piston 53 in the latter. A blind axial passageway 68 extends from the end portion 67 to a place located just below the plate 66. In this region, a radial orifice 69 puts it in communication with the lower chamber 70 of the body 51.

FIG. 15 shows a vessel 71 for preserving a product, for example a food product, under a partial vacuum. This vessel is provided with a hermetically screwed lid 72 provided with a central aperture 73 in which the lower portion 74 of a check-valve or non-return valve 75 is secured. This lower portion comprises a passageway 76 and a planar upper side on which the periphery of an upper member 77 is secured hermetically. The member 77 defines with the portion 74 a cavity for receiving a free planar closure member 76, this cavity communicating upwardly with the exterior by way of a passageway 79 which is cylindrical and then divergent. The upper face of this cavity is planar but grooved.

The lid 72 is also provided with a short vertical pipe 80 having a flange 81. An elastic membrane 82 which is substantially hemispherical caps the pipe 80 and is engaged by its periphery under the flange 81. Further, placed in the vessel 71 is a very flexible elastic small balloon 83 the shape of which is flattened and which contains air under atmospheric pressure, or, possibly, a gas under a pressure slightly lower than the atmospheric pressure.

In order to produce a negative pressure in the vessel 71, which is for example placed on a table, the rod 54 is pulled until it is made to move to the maximum extent out of the body 51 which corresponds to a position of the plate 66 against the end portion 55. The body 51 is held completely in the hand and the end 67 of the rod 54 is applied on the divergent entrance of the passageway 79 and the body 51 is lowered until the end portion 64 of the piston abuts against the spigot 60. In doing so, the air which occupied the volume of the vessel and the passageway 68 occupies in addition practically the whole of the inner volume of the body 51 by raising the closure member 77 and passing through the grooves of its cavity and then through the passageways 79 and 68 and the orifice 69, so that the pressure drops. During this movement, the air which is in the body 51 above the piston 53 is expelled out of the body by way of the vents 61.

As soon as the rod 54 is moved away from the valve 75, the atmospheric pressure hermetically biases the closure member 78 against its lower seat and closes the passageway 76 in a fluidtight manner. Of course it is possible to repeat the operation several times in order to increase the negative pressure in the vessel 71, the value of the latter being limited merely by the degree of sealing of the various component parts. For example, food (rice, wine, etc. . . . ) may be preserved under a partial vacuum in a very simple manner. The working position is particularly convenient since the device can be held in front of oneself roughly at the height of the eyes. Moreover, in order to improve the grip on the device, recesses may be provided for the fingers around the body 51 and/or a recess for the thumb on the top of the cover 52.

As soon as the pressure in the vessel 71 has dropped below a predetermined value, the membrane 82, under the effect of the differential pressure to which it is subjected, becomes hollow under the effect of the suction on its central part in the pipe 80. Simultaneously, or, by way of a modification, when another degree of vacuum is reached, the differential pressure exerted on the balloon 33 inflates the latter and causes it to assume a spherical shape (FIG. 16).

The maintenance of the vacuum is theoretically ensured by the fittings of the lid 72 and by the closure member 78 which may possibly be provided with a cap 84 which is provided with a sealing element 85 and screwed on the entrance of the valve 78 (FIG. 16). However, for various reasons, small leakages may occur and produce the rise in pressure in the vessel 71. In this case, as soon as a certain pressure is reached, the membrane 82 returns to its initial convex shape and/or the balloon 83 collapses. In this way, the user is informed about the pressure prevailing in the vessel at a glance.

Having now described my invention what I claim as new and desire to secure by Letters Patent is:

1. A source of vacuum comprising: a wall laterally defining a tubular body which has a first end portion and a second end portion and an axis and defines an inner chamber, a piston slidable in the body, a rod connected to the piston, an aperture in the body, the rod extending through the aperture, sealing means interposed between the aperture and the rod, means defining a suction orifice located at least in the vicinity of and parallel to said axis, means for depressing the piston toward the second end portion of the body, and communication means for putting the suction orifice suddenly in communication with a part of said chamber in the body which is defined by the first end portion and the piston when the piston is depressed relative to the body toward said second end portion and reaches a predetermined position.

2. A source of vacuum comprising: a wall laterally defining a tubular body which has a first end portion and a second end portion and an axis and defines an inner chamber, two radial ears in the vicinity of the first end portion, an aperture in the body, means defining a suction orifice formed in the second end portion and located at least in the vicinity of and parallel to said axis, a piston slidable in the body, a rod connected to the piston, the rod extending through the aperture, sealing means interposed between the aperture and the rod, means for holding the body and for depressing the piston toward the second end portion of the body in one hand, and communication means for putting the suction orifice suddenly in communication with a part of said chamber in the body which is defined by the first end portion and the piston when the piston is depressed relative to the body toward said second end portion and reaches a predetermined position.

3. A source of vacuum as claimed in claim 2, wherein said communication means comprises a passageway which extends longitudinally in the rod from the piston and terminates in a radial vent which is so disposed as to travel from a side to another side of the first end portion of the body when the piston arrives at said predetermined position.

4. A source of vacuum as claimed in claim 2, wherein said communication means comprises a recess formed on an inner side of said wall of the body and having a dimension axially of the body which exceeds the dimension of the piston axially of the body.

5. A source of vacuum as claimed in any one of the claims 2, 3 or 4, wherein said predetermined position of the piston is a position thereof adjacent the second end portion of the body corresponding to a maximum depression of said piston.

6. A source of vacuum as claimed in any one of the claims 2, 3 or 4, wherein the piston has a peripheral skirt portion which is in contact with said body and extends from the piston toward the second end portion of the body.

7. A source of vacuum as claimed in any one of the claims 2, 3 or 4, wherein the second end portion comprises an end-of-travel abutment for the fully depressed position of the piston.

8. A source of vacuum as claimed in claim 2, wherein said source is coupled with a device for maintaining a negative pressure in an enclosure, the device comprising wall means defining the enclosure, a check-valve having a seat and a closure member associated with and movable relative to said seat, the valve being connected to said wall means, and means for connecting said valve to a source of vacuum and comprising a screwed connector which is associated with the closure member to urge the closure member against the seat when the connector is screwed to the full extent.

9. A source of vacuum as claimed in claim 2, wherein said source is coupled with a device for maintaining a negative pressure in an enclosure, the device comprising wall means defining the enclosure, a check-valve having a valve seat and a closure member associated with and movable relative to the seat, the valve being connected to the wall means, means for connecting the valve to a source of vacuum, an elastically deformable membrane, and means combining the membrane with the enclosure so that the membrane is subjected on a single side of the membrane to a pressure prevailing within the enclosure.

10. A source of vacuum as claimed in claim 9, wherein said combining means define an orifice in said wall means and the membrane has at rest substantially the shape of a hemisphere and has an edge portion which is fixed to a periphery of said means defining the orifice.

11. A source of vacuum as claimed in claim 9, wherein the membrane is constituted by a balloon disposed within the enclosure and having a shape which is flattened under the effect of atmospheric pressure.

12. A source of vacuum as claimed in claim 11, wherein the balloon contains air at atmospheric pressure.

13. A source of vacuum as claimed in claim 11, wherein the balloon contains a gas at a pressure slightly lower than atmospheric pressure.

* * * * *